(12) United States Patent
Zimmermann et al.

(10) Patent No.: US 8,465,955 B2
(45) Date of Patent: Jun. 18, 2013

(54) METHOD FOR ELECTROPORATION OF BIOLOGICAL CELLS

(75) Inventors: Ulrich Zimmermann, Waldbrunn (DE); Vladimir Sukhorukov, Wuerzburg (DE); Kurt Lucas, Hamburg (DE)

(73) Assignee: Eppendorf AG, Hamburg (DE)

( * ) Notice: Subject to any disclaimer, the term of this patent is extended or adjusted under 35 U.S.C. 154(b) by 1518 days.

(21) Appl. No.: 12/072,016

(22) Filed: Feb. 22, 2008

(65) Prior Publication Data

US 2008/0220491 A1    Sep. 11, 2008

Related U.S. Application Data

(62) Division of application No. 10/346,755, filed on Jan. 17, 2003, now Pat. No. 7,358,077.

(30) Foreign Application Priority Data

Jan. 21, 2002 (DE) .................................. 102 02 094

(51) Int. Cl.
*C12M 1/42* (2006.01)
*C12N 13/00* (2006.01)

(52) U.S. Cl.
USPC ............... 435/173.6; 435/285.2; 435/461

(58) Field of Classification Search
None
See application file for complete search history.

(56) References Cited

U.S. PATENT DOCUMENTS

| | | | |
|---|---|---|---|
| 5,883,762 A * | 3/1999 | Calhoun et al. | 205/119 |
| 6,300,108 B1 | 10/2001 | Rubinsky et al. | |
| 6,482,619 B1 * | 11/2002 | Rubinsky et al. | 435/173.7 |
| 6,927,049 B2 | 8/2005 | Rubinsky et al. | |
| 6,936,462 B1 | 8/2005 | Owen et al. | |
| 7,358,077 B2 * | 4/2008 | Zimmermann et al. | 435/285.2 |

FOREIGN PATENT DOCUMENTS

| | | |
|---|---|---|
| WO | WO93/02178 A1 | 2/1993 |
| WO | WO 9966329 A1 * | 12/1999 |
| WO | WO01/07583 A1 | 2/2001 |
| WO | WO01/07584 A1 | 2/2001 |
| WO | WO01/07585 A1 | 2/2001 |

OTHER PUBLICATIONS

Huang, Yong, et al., "Microfabricated electroporation chip for single cell membrane permeabilization"; 2001 Elsevier Science B.V., Sensor and Actuators A 89 (2001) 242-249.

* cited by examiner

*Primary Examiner* — Jeffrey E Russel
(74) *Attorney, Agent, or Firm* — Drinker Biddle & Reath LLP

(57) ABSTRACT

Described are methods for electrical treatment of biological cells, in particular using electrical field pulses, involving the steps: arrangement of the cells (1) on apertures (2) of a solid planar carrier element (3) which divides a measuring chamber (10) into two compartments (11, 12); and temporary formation of an electrical treatment field which permeates the cells, wherein an alternating-current impedance measurement takes place on the carrier element (3), and from the result of the alternating-current impedance measurement, a degree of coverage of the carrier element and/or healing of the cells after electrical treatment are/is acquired. Also described are devices for implementing the methods.

8 Claims, 5 Drawing Sheets

METHOD FOR ELECTROPORATION OF BIOLOGICAL CELLS

CROSS-REFERENCE TO RELATED APPLICATIONS

This is a divisional of U.S. patent application Ser. No. 10/346,755, now U.S. Pat. No. 7,358,077, filed Jan. 17, 2003, which claims benefit of German Application No. DE 102 02 094.9, filed Jan. 21, 2002.

FIELD OF THE INVENTION

The invention relates to methods for electrical treatment of biological cells, in particular for electroporation or electropermeabilisation of biological cells which are arranged on a fixed carrier element, as well as electroporation devices for carrying out such methods.

BACKGROUND

The technique of electroporation (also known as electropermeabilisation, electroinjection or electrotransfection) represents a commonly known means for the inward transfer of membrane-impermeable xenomolecules (e.g. dyes, drugs, hormones, proteins, plasmids etc.) into live cells, or for the controlled release of intracellular substances from the cells. Electroporation has become widely used and recognised because it is more controllable, more reproducible and more efficient than other (chemical or viral) methods of intracellular transport of foreign molecules. The technique of electroporation is based on a temporary increase in membrane permeability which is caused by a reversible electrical breakthrough of the plasma membrane of cells, with the cells being subjected to high-intensity external electrical pulses of very short duration (field intensities of a few kV/cm, pulse duration of some few 10 μsec). The applied electrical field separates charge carriers via the cell membrane so that a transmembrane potential $V_g$ is induced. It is known that the membrane break-through takes place when the induced membrane voltage $V_g$ at room temperature reaches a value $V_g$ of approx. 1 volt.

For freely movable suspended cells, the induced membrane voltage $V_g$ linearly depends on the applied field intensity $E_o$ and on the cell radius a, and follows the generally known integrated Laplace equation:

$$V_g = 1.5 a \cdot E_o \cdot \cos \theta \qquad (1)$$

wherein θ is the angle relative to the direction of the electrical field. If an average value of e.g. 7 μm is used for the cell radius, the minimum critical field intensity $E_{krit}$ which is required for reversible electrical break-through of the membrane regions facing the electrodes (cos θ=1) can be calculated with equation (1): $E_{crit} = Vc/(1.5 \cdot a) \sim 1$ kV/cm. For smaller cells, correspondingly considerably higher field intensities are required to achieve electric break-through through their cell membranes. Thus, for cells with an average radius of e.g. 3 μm, a minimal critical field intensity $E_{crit}$ of approx. 2.5 kV/cm is necessary. As soon as the plasma membrane has been permeabilised by the mechanism of electrical break-through, foreign molecules can enter the cell by way of diffusion (or other mechanisms), or intracellular molecules can flow out into the outside medium. The theoretically calculated values for the critical field intensity $E_{crit}$ correspond very well with experimental results which were determined in electropermeabilisation tests with the use of fluorescent dyes such as propidium iodide or other smaller reporter molecules.

In practical application, efficient electroinjection of macromolecules (proteins, plasmids, DNA etc.) in freely suspended cells requires significantly higher field intensities than those calculated by means of equation (1). Furthermore, the electropermeabilisation yield can be increased by the use of non-physiological media of low conductivity with a low ion content (and reduced osmolarity). However, both very strong electrical fields and media of low conductivity reduce survivability of the cells. In the case of rare or valuable cells (for example genetically modified hybridoma cells or dendritic cells) this can in turn significantly reduce the number of available cells. For this reason, very careful and time-consuming optimisations of the electropermeabilisation protocols are necessary for suspension cells.

The effect of electroporation on cell membranes can be determined directly by measuring their electrical resistance (or the impedance) by means of intracellular electrodes. However, in the case of electroporation of suspended cells, this method is limited to cells of sufficient size (e.g. giant algae, *xenopus oozytes*) and cannot be used on most cells of animal or plant origin which are only a few micrometers in size. The application of extracellular electrodes for measuring the impedance of cell suspensions requires very high cell density (i.e. 30-90% cytocrit value (=cell content of the total suspension)). This method cannot be used for carrying out measurements in diluted cell suspensions (cytocrit<1%), as provided in the electroporation of suspended cells.

It is known to carry out electroporation on embedded cells which are embedded in, or arranged on, micropores of a fixed carrier element made of an electrically insulating material. Electroporation of solid-phase adsorbed cells has the advantage that the electrical flux lines between two electrodes, arranged at opposite sides of the carrier element, are forced to flow through the pores of the carrier element and thus through the cells. From practical application, devices for electroporation of solid-phase adsorbed cells are known, manufactured by Equibio of Great Britain.

For example a device for electroporation and electrofusion of adsorbed biological cells is described in WO 93/02178. A cylindrical chamber is provided which is divided into two compartments by an electrically insulating membrane with through-pores. If pressure is exerted on the liquid, suspended cells are held in place in or on the pores, and exposed to electrical fields which are generated with electrodes in the compartments. While this technique makes possible electroporation and electrofusion in solutions of high or low conductivity, it has, however, the disadvantage in that the arrangement of the cells on the carrier element and the result of electrical treatment cannot be observed or monitored. The device known from WO 93/02178 is thus unsuitable for the treatment, in particular, of rare or valuable cells under practical conditions. The known device has a further disadvantage in that the chamber is combined with a closed pressure system. The design of the device is expensive and handling in practical application is complicated.

Electroporation of individual biological cells in Microsystems and in particular the introduction of an impedance technique are described by Y. Huang et al. in "Sensor and Actuators A", volume 89, 2001, pages 242 ff, and in U.S. Pat. No. 6,300,108 B1. In an electroporation chip which has been produced on the basis of semiconductor materials, the cell is held, by means of liquid pressure, on a connection aperture in a membrane-shaped wall between two compartments. In each of the compartments, electrodes are provided by means of which a poration field can be generated which permeates the fixed cell. Y. Huang et al. describe that the current flow through the carrier element changes, depending on whether the connection aperture is open or occupied by an intact or a permeabilised cell. In order to detect electroporation, the direct current is measured and current-voltage ratios are determined during generation of the poration field, i.e. during permeabilisation of the cell. The poration result can be optically monitored by means of a transparent top of the poration chip.

While the system described by Y. Huang et al. allows real-time monitoring of the poration process, it is, however, not suitable for practical applications in which a multitude of biological cells are to be treated. Furthermore, direct current measuring only provides an information about the membrane characteristics during electroporation, without allowing any further-reaching characterisation of the treated cell for any subsequent processing steps.

Improvements to the poration chip of Y. Huang et al. are described in WO 01/07585, WO 01/07584 and WO 01/07583. These improvements relate in particular to the possibility of treating a multitude of biological cells at the same time. The technique described in the above-mentioned WO publications has the following disadvantages. For real-time monitoring of the poration results, a current measurement is provided at the same time as electroporation. Two measurement and two poration electrodes are provided in the poration chip, thus complicating the design of the poration chip. Real-time monitoring of the poration result covers only commencement of poration and recognition of irreversible damage to the cells. However, this information is insufficient for practical electroporation applications, for example in the field of medicine. Further characterisation of the cells, either before or after electroporation, has to take place with optical means. Optical observation, however, only produces qualitative assessments.

Generally, there is a problem in that only the current is measured in conventional techniques. Electrical measurements supply information that can be evaluated only to a limited extent. There is no specification of measuring parameters that furnish reliable measuring results. However, the measuring object comprising electrolyte and biological cell in the measuring chamber is a complicated structure characterised by capacities and resistances which, depending on the type of cells to be treated, requires other measuring parameters.

OBJECT OF THE INVENTION

It is the object of the invention to provide improved methods for the electrical treatment of biological cells, in particular for the treatment of biological cells by means of electrical field pulses, with which methods the disadvantages of conventional methods can be overcome, and with the methods in particular making possible reproducible real-time monitoring of the entire treatment, including monitoring of the preparatory steps and/or of the treatment result. In particular, the invention is to permit faster and more accurate optimisation of electroporation protocols for special cell types. It is also the object of the invention to provide devices for implementing the methods, in particular, methods for treating biological cells using electrical field pulses, wherein the devices are to make possible complete and reproducible observation of the treatment process and result.

SUMMARY OF THE INVENTION

The basic idea of the invention consists of further developing conventional methods for electrical treatment of biological cells which are solid-phase adsorbed on a carrier element, to the effect that on the carrier element an alternating-current impedance measurement to determine the degree of coverage of the carrier element and/or the electrical characteristics of the cells, either before or after electrical treatment, takes place. The alternating-current impedance is the complex, frequency-dependent alternating-current resistance of the system under consideration which comprises resistive, capacitive and/or inductive characteristics. There are two aspects to the measures mentioned. On the one hand, for the first time true impedance measuring is carried out which, apart from a statement on the electrical resistance of the cells, advantageously supplies additional information about capacitive characteristics of the cells. Impedance measuring has the particular advantage in that it supplies frequency-dependent measuring results. In particular, it is possible to determine in one test the optimal measuring frequency and/or a measuring frequency at which frequency minimal damage to the measured cells or cell components occurs. These advantages were not provided in the case of conventional direct-current measurements. The inventors have recognised that conventional measurements neglect the capacitive influences of the cells. Furthermore, impedance measuring according to the invention does not take place during electrical treatment but before or after application of the respective electrical field pulses to the cells. Reproducible quantitative parameters of the cells and of the carrier element, in particular of the degree of coverage of the carrier element, and if need be the deformation of the cells in the solid-phase adsorbed state and the result of cell treatment, are acquired. Advantageously, the methods according to the invention allow cell-type-specific, reproducible and gentle treatment of a multitude of cells such as is required for example in biochemistry or medicine.

The solid-phase adsorbed cells which have been treated and measured according to the invention comprise cells which have been applied from the suspended state onto a fixed carrier, if need be under the effect of a liquid pressure, or comprise adherent cells. Adherent cells have grown or have been cultivated on the carrier element prior to treatment and measurement. Advantageously, mechanical prestressing of cells by applying negative pressure to increase electropermeabilisation is also possible in the case of adherent cells.

According to a particularly advantageous embodiment of the invention, alternating-current impedance measuring takes place at a predetermined measuring frequency which is optimised in a cell-type specific way in relation to the acquisition of as pronounced a measuring signal as possible. Preferably, the measuring frequency is determined by a preliminary test which comprises picking up a frequency dependence in the alternating-current impedance of solid-phase adsorbed cells. Determining an optimal measuring frequency represents an important advantage when compared to conventional direct-current measuring, because the invention allows the setting of measuring parameters which are as gentle as possible. According to the invention, measuring voltages can be used whose amplitudes are reduced in comparison to the conventionally used measuring voltage.

Another subject of the invention is a device for electrical treatment of biological cells, in particular an electroporation device which is provided with an alternating-current impedance measuring device. According to a preferred embodiment of the device according to the invention, a measuring chamber is divided into two compartments by means of a fixed carrier element comprising a multitude of through-apertures, with one electrode being provided in each compartment, said electrode being optionally adapted for impedance measuring or for electrical treatment of cells on the carrier element. In contrast in particular to conventional poration chips, advantageously only one pair of electrodes is provided in the measuring chamber, with said pair of electrodes being used doubly for measuring and treatment purposes. According to a further advantageous aspect, the device according to the invention is not connected to a closed pressure system. The upper compartment of the measuring chamber is exposed to ambient pressure.

The invention has the following advantages. For the first time, a method suitable for routine application of electrical treatment of biological cells is available. Both the degree of permeabilisation of the cells and the kinetics of the healing of cells after treatment (resealing) can be acquired. By means of impedance measuring which lasts until after treatment, it is possible to monitor the number of cells that heal. This allows control over the entry of substance from the suspension to the cells. Advantageously, according to the invention, not all apertures (pores) of the carrier elements need be occupied by cells. Impedance measuring according to the invention allows quantitative statements even if the carrier element is partly occupied. Advantageously, the method according to the invention can be integrated in further standard procedures for cell treatment. For example, cultivation of the treated cells can follow immediately after electrical treatment. The device according to the invention makes it possible to simultaneously carry out electrical and optical monitoring of the treatment result and the healing process. The design of the measuring chamber used according to the invention is simplified when compared to conventional devices.

In contrast to conventional electropermeabilisation methods which use very high field intensities and input voltages, if need be, the method according to the invention works with middle or even low input voltages. This is possible because, as a result of the arrangement according to the invention, of the carrier element, the applied field is forced to flow through the cells embedded in the pores. This encourages charging and break-through of the cell membrane. Furthermore, the low hydrostatic negative pressure to which the cells are exposed causes deformation of the cells in the direction of the field. Advantageously, as illustrated below, this additional mechanical stress results in further improvement of the electropermeabilisation yield. A further advantage of the invention consists of electropermeabilisation being able to be carried out in physiological media, i.e. in media rich in salt. In contrast, conventional methods for electropermeabilisation of suspension cells are carried out predominantly in media of low conductivity, because permeabilisation in such media with a lower ion content takes place more efficiently. By using physiological media in combination with the mechanical support provided by the carrier element, the survivability of the cells after electropermeabilisation is increased significantly, without having a significant influence on the electropermeabilisation yield.

BRIEF DESCRIPTION OF THE DRAWINGS

Further advantages and details of the invention are stated in the description of preferred embodiments which are illustrated in the enclosed drawings, with the following being shown.

DESCRIPTION OF THE PREFERRED EMBODIMENTS

The invention is generally applicable in electromanipulation techniques in which biological cells or cell components are exposed to electrical field pulses, for example to carry out the above-mentioned permeabilisation of the cell membrane or some other temporary or permanent treatment of the cell. Below, the invention is described using the example of electroporation of biological cells, without there being any limitation to this particular application. For practical application, there is an interest in treating a multitude of cells at the same time. However, the invention also relates to the special application case where only single cells are to be subjected to electrical treatment.

Figure 1:
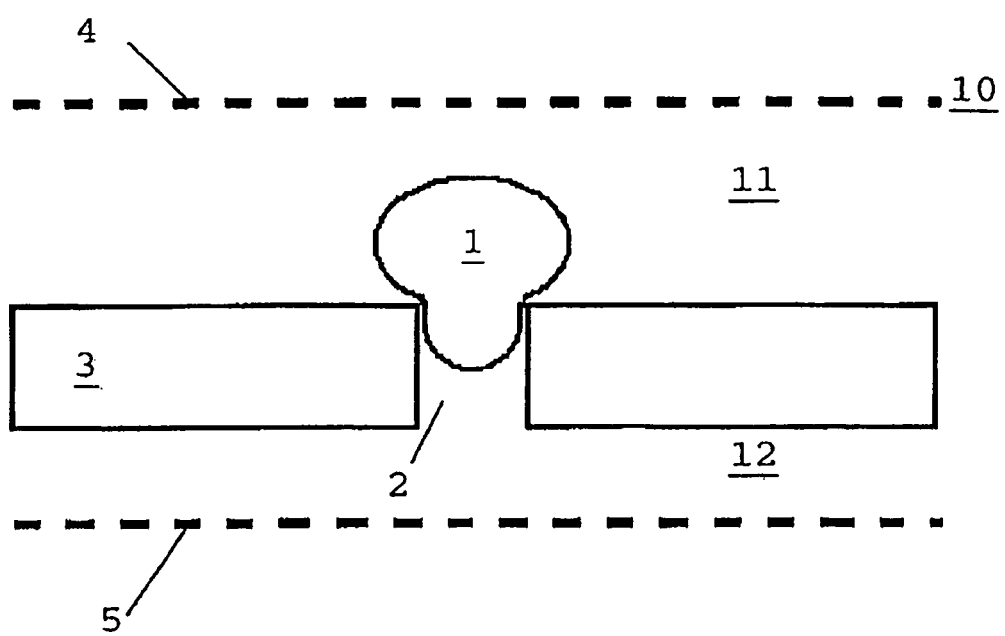
FIG. 1 a diagrammatic partial view of the design of a measuring chamber used according to the invention.

FIG. 1 is a diagrammatic partial section view of the basic constituents of the measuring chamber of an electroporation device according to the invention. The measuring chamber 10 is divided into two compartments 11, 12 by a planar carrier element 3 made from an electrically insulating material, with an upper electrode 4 and a lower electrode 5 being arranged in each of said compartments. The measuring chamber 10 is connected to a liquid-line system and a measuring and control device which are shown as an example in FIG. 2. The carrier element 3 comprises at least one through-aperture 2 by way of which the compartments 11, 12 are connected with each other. Many apertures 2 are provided for the treatment of a multitude of cells. Generally, one cell 1 is arranged on one pore 2 (as shown) or distributed over several pores. For example, a cell can extend across approximately 20 to 50 pores in the carrier element 3. The cells have been applied to the carrier element 3 from a suspension or by growth.

As shown, the apertures 2 are formed as through-pores. As an alternative, the carrier element 3 can be made from a material which is porous per se, said material ensuring a liquid connection and thus pressure compensation between the compartments 11, 12. For implementing through-apertures or pores 2, the carrier element 3 is preferably flat, plate-shaped, disk-shaped or membrane-shaped. If porous material is used, the carrier element 3 can however as an alternative be volume-shaped. In this case, the lower electrode 5 can be situated directly on the underside of the carrier element 3.

According to a preferred embodiment of the invention, the carrier element 3 is formed by a membrane filter comprising electrically high-insulating material. For example, a commercially available membrane filter comprising polycarbonate, silicon nitride or another electrically insulating material with a predetermined pore size and pore distribution is used. Preferably a membrane filter with cylindrical micropores of a diameter which is smaller than the diameter of the cells 1 to be treated is selected, the diameter ranging for example from 0.01 μm to 8 μm.

The electrodes 4, 5, are optically at least partly transparent. They consist for example of a wire mesh which, if necessary, is affixed to a transparent carrier, or a transparent conductive material, such as ITO (indium tin oxide). The electrodes 4, 5 can carry out several tasks. On the one hand, they serve as measuring electrodes for monitoring the occupation of the aperture(s) 2 with cells 1 prior to electroporation, and for monitoring the progress of membrane permeabilisation and healing of the cell membranes after pulse application by way of continuous impedance measurements. On the other hand, said electrodes 4, 5 serve as poration electrodes for applying electrical field pulses. The transparent electrodes 4, 5 allow optical control of the arrangement of the cells on the carrier element 3 and of the progression of electroporation. Optical control preferably takes place with a microscope, which is arranged above the measuring chamber 10, using fluorescent dyes.

Figure 2:
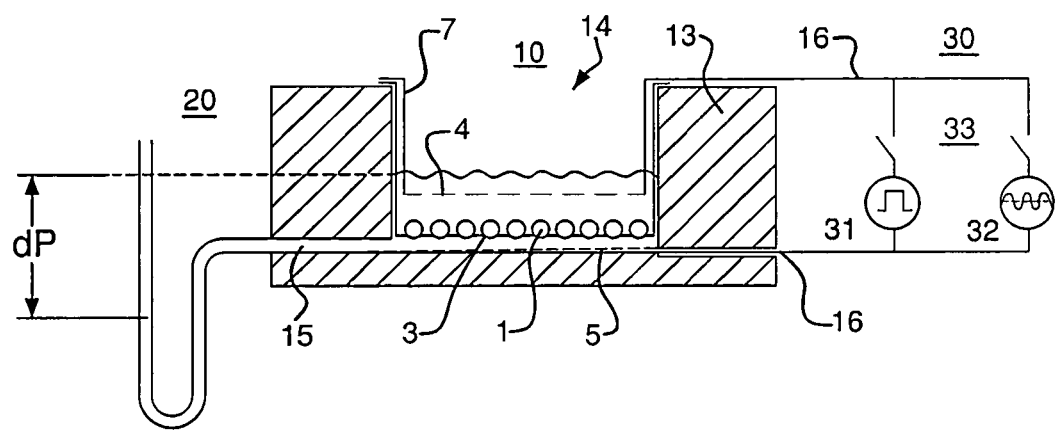
FIG. 2 a sectional view of a preferred embodiment of a device according to the invention.

FIG. 2 diagrammatically shows further details of the poration device according to the invention. The measuring chamber 10 is formed in a container 13 comprising a cylindrical interior space 14, a liquid-line system 15 and electrical connection lines 16. The container preferably comprises transparent plastic, e.g. PMMA. The carrier element 3 divides the interior space 14 into an upper and a lower compartment 11, 12. The carrier element 3 extends as a planar wall across the cross section of the measuring chamber 10. Said carrier element 3 is connected to the interior walls of the container 13 or preferably (as shown) hooked into the container 13. To this purpose, a cylindrical tissue culture insert 6 (e.g. manufacturer: Nunc, diameter 25 mm) is used to which a polycarbonate filter (pore size e.g. 8 μm) is attached as a carrier element 3. Preferably, the electrode 4 of the upper compartment 11 is also hooked into the container 13 or is detachably attached to the upper rim of said container 13. For example a stainless steel mesh with a mesh width of approx. 50 μm on a fixing device 7 is provided as an electrode 4. The lower electrode 5 is arranged at the bottom of the container 13; it also comprises a stainless steel wire mesh. The vertical distance between the mesh electrodes 4, 5, which are stretched across in a planar arrangement, is e.g. 1 mm. The measuring chamber 10 is connected to a diagrammatically illustrated pressure device by way of the liquid-line system 15. By means of the pressure device 20, slight negative pressure is exerted on a liquid contained in the measuring chamber 10. Advantageously, negative pressure of some few cm water column (e.g. 30 mbar) in relation to the ambient pressure is sufficient.

The electrodes 4, 5 are connected with a measuring and control device 30. The device 30 comprises a pulse generator 31 and an impedance measuring device 32 which optionally are alternately or simultaneously connected to the electrodes 4, 5 by way of a switching device 33. For example, a multiporator (manufacturer: Eppendorf AG, Hamburg, Germany) is used as a pulse generator 31; it is controlled by a microprocessor unit. The multiporator generates exponentially decreasing field pulses with amplitudes of up to 1.2 kV and time constants ranging from 15 to 500 μs. By way of the microprocessor unit, the pulse conditions can be set with high reproducibility, irrespective of any variations in the ion composition of the pulse medium (of the suspension in the measuring chamber) or irrespective of any changes in the conductivity of the medium, as can occur as a result of ion flows from the cytosol or as a result of cell lysis during pulse application. The impedance measuring device 32 is preferably an impedance analyser (e.g. HP 4191A, manufacturer: Hewlett Packard, USA) which allows impedance measuring in a frequency range of 100 Hz to 13 MHz.

According to a preferred embodiment of the invention, the switching device 33 is a switch with which either the pulse generator 31 or the impedance measuring device 32 is connected to the electrodes 4, 5. Depending on the application, it is, however, also possible to provide for a permanent electrical connection between the impedance measuring device 32 and the electrodes 4, 5, wherein the switching device 33 merely serves to activate the pulse generator 31 and to apply the field pulses to the adsorbed cells 1. In this configuration, impedance measuring can also be continued during treatment of the cells.

Implementation of the invention is not limited to the components of the device 30 which have been given as examples. As far as the pulse generator is concerned, it is also possible to use another generator of the type known per se, which supplies the pulses required for the respective treatment of cells. As far as the impedance measuring device is concerned, any measuring device, e.g. based on a measuring bridge, can be used which makes it possible to fully measure the alternating-current resistance.

Different from the arrangement shown in FIG. 2, a device, according to the invention, for treating biological cells can also be constituted by a container in which a multitude of measuring chambers are provided. Each measuring chamber is designed analogous to that of FIG. 2. Pressure control and pulse control of the measuring chambers can be provided together or individually.

Figure 3:
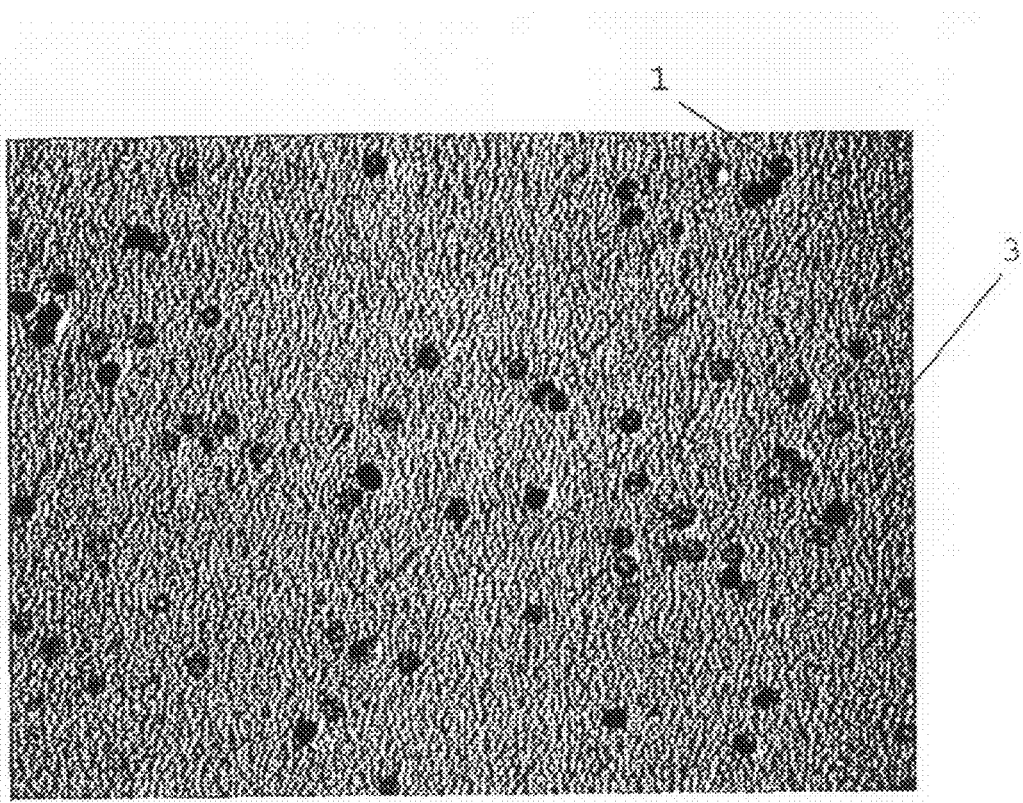
FIG. 3 a microscopic view of a carrier element.

To carry out a method according to the invention, the measuring chamber 10 is filled with a pulse medium. The pulse medium is e.g. a saline solution with a conductivity that has been set depending on the application. Advantageously, according to the invention, an isoosmolar pulse medium is used in which the electrical treatment of the cells takes place in a particularly gentle manner. Subsequently, a suspension of the cells to be treated is pipetted in from above. Advantageously, this can take place via the upper electrode. If, according to a preferred embodiment, the measuring chamber 10 is open at the top, feeding-in of the cell suspension can take place with any pipetting device known per se. As an alternative, the cells can have been grown on the carrier element 3 in a prior process. Subsequently, negative pressure is applied by the pressure device 20, so that with the suspension, the cells 1 are drawn to the carrier element 3 where they are fixed at the apertures 2. Under the influence of the negative pressure, the cells 1 are slightly drawn into the pores 2 (see FIG. 1). FIG. 3 shows a carrier element 3. The density of the carrier element 3 is for example $10^8$ apertures (or pores) per $cm^2$.

Subsequently, the impedance is measured to determine the degree of coverage with cells, of the carrier element 3, followed by electrical treatment of the cells by means of poration pulses, and by impedance measurement for monitoring healing of the permeabilised cell membranes. Below, these process steps are illustrated with reference to one application example.

APPLICATION EXAMPLE

Cells

The mouse myeloma cell line Sp2 was cultivated in the RMPI 1640 Complete Growth Medium (CGM) with 10% FCS (Fetal Calf Serum, PAA, Linz, Austria) at 37° C. under 5% CO2. The cells were kept in the exponential growth phase by subcultivation three times per week. Prior to commencement of electropermeabilisation, the cells were washed once or twice in pulse medium and resuspended in the pulse medium 10 min prior to pulse application. The average cell diameter was determined by electronic size determination by means of CASY (Schärfe Systems, Reutlingen, Germany) at approx. 14 μm.

Pulse Media

A phosphate buffer comprising 1.15 mM K2HPO4/KH2PO4 buffer, pH 7.2 was used as a pulse medium. KCl at a concentration of 10 and 30 mM respectively was added as a conducting salt. Osmolarity was set to 290 mOsm by adding Inositol, so as to obtain an isoosmolar solution.

Impedance Measurement Prior to Electroporation

Figure 4A:
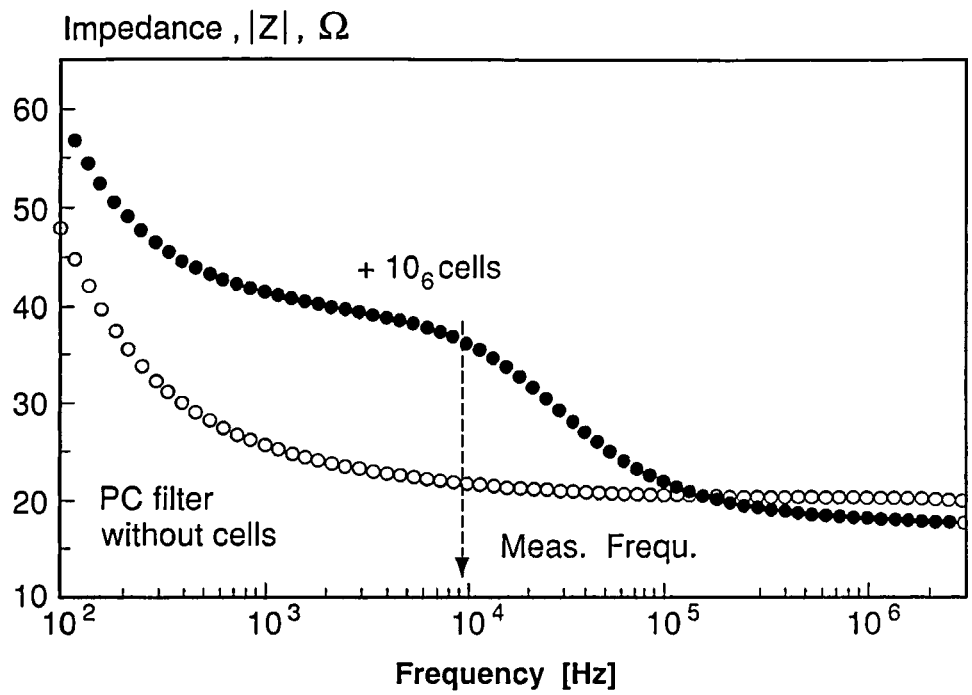
FIGS. 4A, 4B, 5A, 5B graphs illustrating impedance measurements according to the invention.

FIG. 4A shows impedance spectra of the measuring chamber filled with pulse medium, with and without the addition of a cell suspension. The measuring chamber was filled with an isoosmolar pulse medium of low conductivity (1.25 mS/cm, 290 mOsm, pH 7.4) with the impedance being determined via the frequency range of 100 Hz to 2.5 MHz (outline symbols).

The impedance remained relatively constant over a large frequency range (1 kHz-1 MHz) at a value of approx. 20Ω. At lower frequencies (<1 kHz) there was a clear increase in the impedance as the frequency decreases, such increase is believed to have been due to electrode polarisation processes. After the addition of $10^6$ Sp2 cells and subsequent embedding of the cells in the pores 2 by means of the externally applied negative pressure (approx. 30 mbar), there was a clear increase in the impedance (closed symbols). During the following impedance measurements, the negative pressure remained. Increased impedance when applying the cells to the carrier element 3 corresponds to the increase, known per se, in the alternating-current resistance between the electrodes as a result of an interruption in the electrolyte connection between the compartments and the pores occupied with cells.

The inventors have found that the impedance increase depends on the measuring frequency. For this reason, according to a particularly advantageous embodiment of the method according to the invention, prior to the actual treatment, a preliminary test is provided during which, in a cell-type specific way, the optimum measuring frequency is determined, at which frequency the impedance increase during occupation of the pores by cells is particularly pronounced. Accordingly, the subsequent measurements are carried out at the optimum measuring frequency as determined in advance. It can also be provided for the impedance measurement device to be set to a predetermined measuring frequency which, from tabular values or the like, is determined to be the optimal value.

In the example shown, subsequent measurements were carried out at a frequency of 10 kHz, since at this frequency the difference between the occupied and unoccupied filter membrane, and thus sensitivity, was largest (arrow in FIG. 4A). The clear increase in impedance in the frequency range between $10^3$ and $10^5$ Hz is due to the micropores being occupied by cells which themselves have insulating characteristics (in this frequency range) and which close the pore apertures so that the alternating-current resistance of the entire arrangement increases.

Figure 4B:
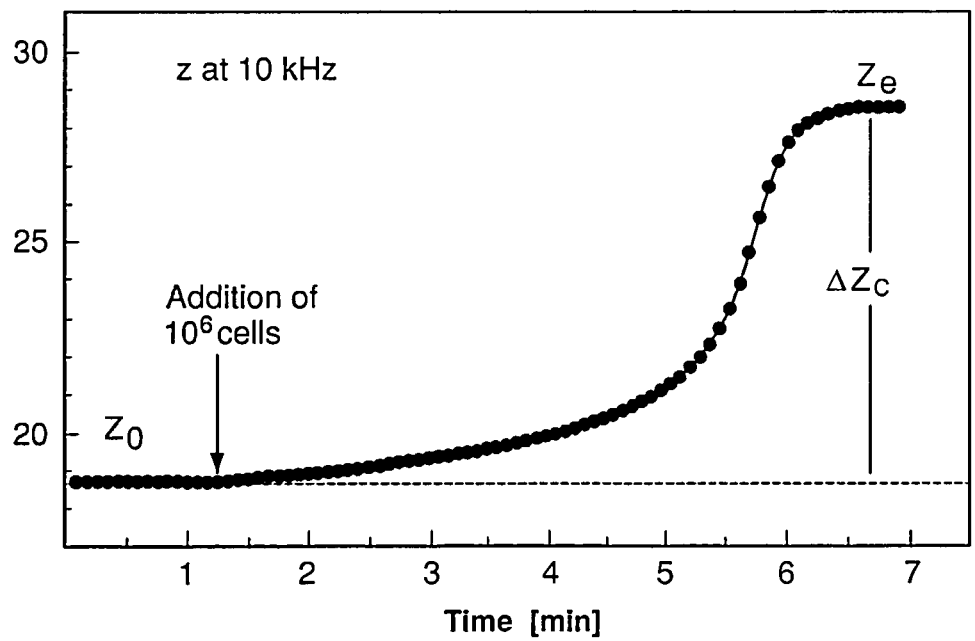

FIG. 4B shows the progression over time of the occupation of the carrier element 3 with cells 1. The chamber was filled with the pulse medium and the impedance was measured at 10 kHz ($Z_0 \approx 19\Omega$). After 75 s (see arrow) $10^6$ cells were added and embedded in the pore apertures (see FIG. 4A). After this point in time, there was a continuous increase in the impedance which after approx. 6 min turns to saturation ($Z_0 \approx 28$). This increase in the impedance is due to increased occupation of pores by cells, an increase which reaches its maximum at $Z_e$. The increase in the impedance, caused by the occupation of micropores by cells, is designated $\Delta Z_c$.

The sigmoid shape according to FIG. 4B corresponds to the time gradient of occupation of the pores 2 with cells 1. Immediately after the cells have been added there are only relatively few cells in the direct surroundings of the pores, which cells can close off these pores, so that at first there is only a slight increase in the impedance. As a result of the negative pressure applied, as time goes on more and more cells which were originally situated in regions further afield are moved to the pores and close said pores. This is shown in the rapid increase of the resistance. Finally, when the maximum number of cells occupies the membrane, the impedance reaches a saturation value ($Z_e$). The difference $\Delta Z_c$ between this end value $Z_e$ and the start value $Z_o$ (chamber without cells) is achieved by adding the cells. The difference is thus an exactly determinable measure for the occupation of the membrane with cells, i.e. for the degree of coverage of the carrier element. The degree of coverage corresponds to the share of pores which are occupied with cells. At maximum coverage, the degree of coverage is 1.

It must be pointed out that the alternating-current impedance determined according to the invention is generally a complex value. The absolute value of impedance illustrated in the figures contains both amplitude information and phase information. Correspondingly, as a physical value it must be differentiated from conventionally measured power-voltage ratios.

When implementing the method according to the invention, depending on the application, determination of the degree of coverage of the carrier element 3 by determining the overall kinetics which is shown in FIG. 4B is provided for, or measuring an actual impedance, with calculation of the actual coverage from this impedance value and from comparison values is provided for. From the degree of coverage and the geometric parameters of the carrier element used, the number of cells which are subsequently treated by electroporation can be determined.

Impedance Measurements During or After Electroporation

Figure 5A:
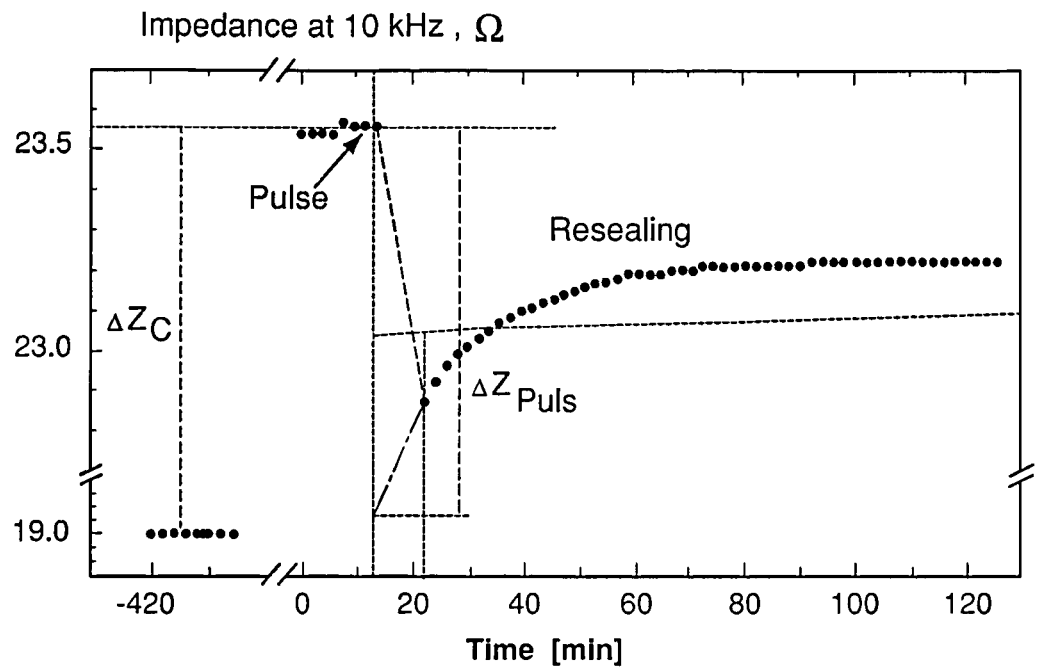
Figure 5B:
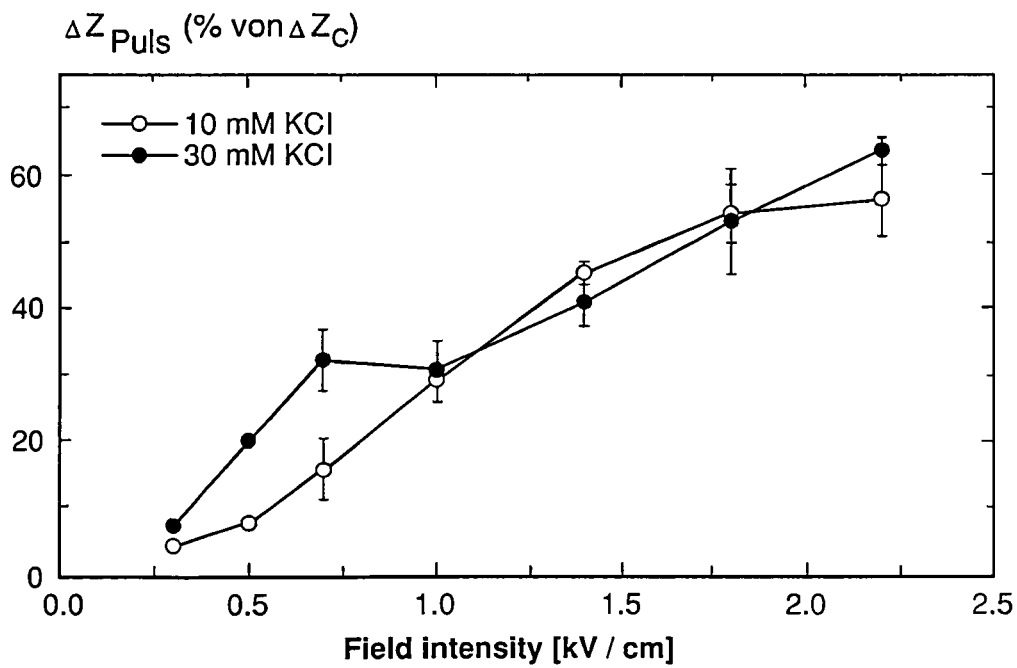

FIGS. 5A and 5B illustrate the impedance measurements during and after electroporation. The left part of FIG. 5A shows the impedance increase as a result of the occupation of pores shown in FIG. 4B. After maximum occupation of the pores was attained, impedance measuring was temporarily interrupted while a pulse of 1 kV/cm field intensity and 40 µs pulse duration (see arrow) was applied with the pulse generator 31 (see FIG. 2). Impedance measuring was then continued and at first a clear decrease in the resistance immediately following pulse application was evident. This can be explained by the loss of insulating characteristics of the cells, such loss being caused by the pulse-induced break-through of the cell membranes. Thus, the electroporation device according to the invention provides an opportunity of quantitatively registering the electrical membrane break-through by means of impedance measurement in the seconds range. The impedance then continually increased, following exponential kinetics, until after approx. 2 min the original value was almost reached again. This resealing or healing kinetics can be described by an exponential saturation of the first order so that the maximum pulse-induced impedance change $\Delta Z_{Puls}$ can be determined relatively precisely by way of extrapolation. The increase in the impedance to almost the value prior to pulse application reflects resealing of the cells. In other words, during this time the membrane disturbances of the cells heal, and the cell regains its insulating characteristics, a situation shown in the increase of the resistance. Furthermore, the impedance gradient can also be used to determine the share of any irreversibly permeabilised, i.e. dead, cells. The combined impedance and pulse arrangement also makes it possible to quantitatively measure the entire progression of electropermeabilisation in a single chamber over a relatively extended time period. The impedance kinetics or at least the individual impedance values, which are referenced using reference values, characterise the healing of the cells.

FIG. 5B shows the influence the field intensity has on the pulse-induced impedance change: electroporation experiments with pulse durations of 40 µs and with field intensities ranging from 0.3 to 2.2 kV/cm in pulse media of various ion compositions (10 mM KCl (1.25 mS/cm; outline symbols) and 30 mM KCl (3.5 mS/cm; closed symbols)) respectively were carried out and evaluated (see above). The values determined in this way for the pulse-induced impedance change $\Delta Z_{Puls}$ were standardised to the respective impedance of the membrane filter $\Delta Z_c$ occupied by cells. The average values of these standardised pulse-induced impedance changes (±standard deviations) from 3 to 5 experiments each, were plotted. The values increase with an increase in the field intensity which is due to an increased number of permeabilised cells. Electropermeabilisation in media of superior conductivity (closed symbols) shows a progression which is similar to that in media of lesser conductivity (outline symbols).

FIG. 5B shows a particular advantage of the invention. Clear effects of the electrical field pulse are already evident at field intensities which are below the theoretically calculated field intensities and field intensities stated in the literature, in relation to freely suspended cells. The reasons for this lowering of the critical field intensity are due on the one hand to "concentration" of the electrical field in the region of the filter pores; and on the other hand to an additional mechanical prestressing of the cell membrane in the field direction, such prestressing being due to the negative hydrostatic pressure. Both the mechanical stress and the electromechanical deformation force have a strong influence on the permeabilisation of cells.

In electroporation devices according to the invention, efficient permeabilisation is also possible in isoosmolar media of increased conductivity. This is shown in the comparison of the two pulse media in FIG. 5B. As already mentioned, isoosmolar media with good conductivity favour the survivability of electropermeabilised cells. Thus, this arrangement makes possible efficient electropermeabilisation while at the same time ensuring good vitality, even in isoosmolar media rich in salt.

Further Processing Steps

According to the invention, evaluation of the treatment results can be followed by further electrical treatment with a changed pulse medium or cultivation of the treated cells. A particular advantage of the modular design of the device according to the invention consists of the possibility of removing the carrier element from the measuring chamber and transferring it to a cultivation apparatus. In the cultivation apparatus the treated cells are cultivated. Cultivation can also take place in the measuring chamber itself.

The characteristics of the invention disclosed in the above description, in the claims and in the drawings, can be of significance for implementing the invention in its various embodiments, both individually and in combination.

We claim:

1. A method for electrical treatment of biological cells using electrical field pulses comprising the steps of:

arranging the cells on apertures of a solid planar carrier element which divides a measuring chamber into two compartments, said carrier element being covered with said cells with a degree of coverage;

temporarily forming an electrical treatment field which permeates the cells, measuring an alternating-current impedance on the carrier element, wherein the measuring step is at a predetermined measuring frequency at which frequency the alternating-current impedance measured on the carrier element is increased to its maximum as a result of the arrangement of the cells, and determining said degree of coverage of the carrier element or a degree of healing of said cells after said electrical treatment, or both from the result of said alternating-current impedance measurement.

2. The method according to claim 1, wherein the measuring step includes measuring an alternating current impedance kinetic and measuring at least one impedance value.

3. The method according to claim 2, wherein said degree of coverage of the carrier element is determined by said measuring the alternating-current impedance kinetic during arrangement of the cells on the apertures of the carrier element, or by measuring the at least one impedance value, and calculating the degree of coverage from at least one comparison value.

4. The method according to claim 2 wherein said degree of healing is determined by said measuring the alternating-current impedance kinetic after electrical treatment of the cells or by measuring the at least one impedance value at at least one predetermined point in time, and comparing with at least one reference value.

5. The method according to claim 1, wherein said measuring frequency is determined by a preliminary test in which a frequency dependence of the alternating-current impedance is determined from at least one reference value.

6. The method according to claim 1 further comprising observing optically, with a microscope, the arrangement of the cells and the result of the electrical treatment.

7. The method according to claim 1 wherein the arranging step comprises adsorbing said cells from a suspension or an adherent growth of said cells.

8. The method according to claim 1 further comprising cultivating said cells on the carrier element after the forming step.

* * * * *